US00PP26449P2

(12) United States Plant Patent
Hooijman

(10) Patent No.: US PP26,449 P2
(45) Date of Patent: Mar. 8, 2016

(54) ROSE PLANT NAMED 'ESM R059'

(50) Latin Name: *Rosa hybrida*
Varietal Denomination: ESM R059

(71) Applicant: Aloysius A. J. Hooijman, Aalsmeer (NL)

(72) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 120 days.

(21) Appl. No.: 13/987,846

(22) Filed: Sep. 9, 2013

(51) Int. Cl.
*A01H 5/02* (2006.01)

(52) U.S. Cl.
USPC ..... Plt./150

(58) Field of Classification Search
USPC ..... Plt./150
See application file for complete search history.

(56) References Cited

PUBLICATIONS

UPOV hit for Rose 'ESM 059' QZ PBR 20112026, www.upov.int., application date Aug. 25, 2011, published Oct. 15, 2011.*

* cited by examiner

*Primary Examiner* — Anne Grunberg
(74) *Attorney, Agent, or Firm* — C. A. Whealy

(57) ABSTRACT

A new and distinct cultivar of Rose plant named 'Esm R059', characterized by its upright and strong flowering stems; vigorous growth habit and high productivity; freely flowering habit; light red-colored flowers that are typically grown as spray types; excellent postproduction longevity; and resistance to *Botrytis*.

1 Drawing Sheet

Botanical designation: *Rosa hybrida*.
Cultivar denomination: 'ESM R059'.

BACKGROUND OF THE INVENTION

The present Invention relates to a new and distinct cultivar of Rose plant, botanically known as *Rosa hybrida*, commercially used as a cut flower Rose plant, typically referred to as a floribunda type, and hereinafter referred to by the name 'Esm R059'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in July, 2007 of a proprietary Rose selection identified as Line 188, not patented, as the female, or seed, parent with a proprietary Rose selection identified as Line 222, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in October, 2008.

Asexual reproduction of the new Rose plant by bud grafting in El Quinche, Pichincha, Ecuador since February, 2009 has shown that the unique features of this new Rose plant are stable and reproduced true to type in successive generations of asexual reproduction.

SUMMARY OF THE INVENTION

Plants of the new Rose have not been observed under all possible environmental conditions and cultural practices. The phenotype may vary somewhat with variations in environmental conditions such as temperature and light intensity, without however, any variance in genotype.

The following traits have been repeatedly observed and are determined to be the unique characteristics of 'Esm R059'. These characteristics in combination distinguish 'Esm R059' as a new and distinct Rose plant:

1. Upright and strong flowering stems.
2. Vigorous growth habit and high productivity.
3. Freely flowering habit.
4. Light red-colored flowers that are typically grown as spray types.
5. Excellent postproduction longevity.
6. Resistant to *Botrytis*.

Plants of the new Rose differ from plants of the female parent selection in the following characteristics:

1. Plants of the new Rose are taller than plants of female parent selection.
2. Plants of the new Rose are more vigorous than plants of female parent selection.
3. Stems of plants of the new Rose have fewer thorns than stems of plants of the female parent selection.
4. Plants of the new Rose have longer flower buds than plants of the female parent selection.

Plants of the new Rose differ from plants of the male parent selection in the following characteristics:

1. Plants of the new Rose are shorter than plants of the male parent selection.
2. Plants of the new Rose are more vigorous than plants of the male parent selection.
3. Stems of plants of the new Rose have fewer thorns than stems of plants of the male parent selection.

Plants of the new Rose can be compared to plants of Rose 'Babe', not patented. In side-by-side comparisons conducted in El Quinche, Pichincha, Ecuador, plants of the new Rose differed from plants of 'Babe' in the following characteristics:

1. Plants of the new Rose were shorter and broader than plants of 'Babe'.
2. Plants of the new Rose were more vigorous than plants of 'Babe'.
3. Plants of the new Rose had shorter internodes than plants of 'Babe'.
4. Plants of the new Rose had stronger stems than plants of 'Babe'.
5. Stems of plants of the new Rose had fewer thorns than stems of plants of 'Babe'.
6. Plants of the new Rose had broader flower sprays with more flowers per spray than plants of 'Babe'.
7 Plants of the new Rose flower later than plants of 'Babe'.
8. Flowers of plants of the new Rose were longer lasting than flowers of plants of 'Babe'.
9. Plants of the new Rose and 'Babe' differed slightly in flower color.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the upper left of the sheet comprises a side perspective view of typical flowering stem of 'Esm R059'.

The photograph at the upper right of the sheet is a close-up view of a typical flowering stem of 'Esm R059'.

The photograph at the lower left of the sheet is a close-up view of a typical flower of 'Esm R059'.

The photograph at the lower right of the sheet are close-up views of the upper and lower surfaces of typical leaves of 'Esm R059'.

DETAILED BOTANICAL DESCRIPTION

Plants of the new Rose have not been observed under all possible environmental conditions and cultural practices. The phenotype may vary somewhat with variations in environmental conditions such as temperature and light intensity, without, however, any variance in genotype. The aforementioned photographs, following observations and measurements describe plants grown in beds in a polyethylene-covered greenhouse in El Quinche, Pichincha, Ecuador and under typical hydroponic Rose production practices. Plants were pinched 13 to 14 weeks after planting and were 77 weeks old when the description and photographs were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'Esm R059'.

Parentage:

*Female, or seed, parent*.—Proprietary seedling selection of *Rosa hybrida* identified Line 188, not patented.

*Male, or pollen, parent*.—Proprietary seedling selection of *Rosa hybrida* identified Line 222, not patented.

Propagation:

*Type*.—By bud grafting.

*Time to initiate roots*.—About seven to ten days at 26° C. to 30° C.

*Time to produce a rooted young plant*.—About four to five weeks at 22° C. to 26° C.

*Root description*.—Fibrous, medium in thickness; close to 199A in color.

*Rooting habit*.—Moderately freely branching; sparse.

Plant description:

*Plant and growth habit*.—Perennial shrub; upright and strong flowering stems; typically grown as a spray-type cut flower; vigorous growth habit.

*Branching habit*.—Freely basal branching habit; highly productive with about 9.6 flowering stems developing per plant per year.

*Plant height*.—About 111 cm.

*Plant width* (*spread*).—About 64 cm.

*Lateral branches*.—Quantity: About 19 lateral branches develop per plant. Length: About 85 cm. Diameter: About 8 mm. Internode length: About 4.5 cm. Texture: Smooth, glabrous; older stems, woody. Color: Close to 146B and becoming closer to 200C with development. Thorns: Density: Sparse. Shape: Triangular with sharp acuminate apices; slightly incurved. Height: About 8 mm. Length, at base: About 8 mm. Color, immature: Close to 53A. Color, mature: Close to 183C.

Leaf description:

*Arrangement*.—Alternate; compound with typically seven to nine leaflets per leaf.

*Leaf length*.—About 17.9 cm.

*Leaf width*.—About 11.5 cm.

*Terminal leaflet length*.—About 5.9 cm.

*Terminal leaflet width*.—About 4.2 cm.

*Lateral leaflet length*.—About 5.5 cm.

*Lateral leaflet width*.—About 3.6 cm.

*Leaflet shape*.—Ovate.

*Leaflet apex*.—Acute.

*Leaflet base*.—Attenuate.

*Leaflet margin*.—Serrate.

*Leaflet texture, upper and lower surfaces*.—Smooth, glabrous; coriaceous.

*Leaflet venation pattern*.—Pinnate.

*Leaflet color*.—Developing leaflets, upper surface: Close to 139A and 187A. Developing leaflets, lower surface: Close to 148A and N199B. Fully expanded leaflets, upper surface: Close to 139A; venation, close to 183B. Fully expanded leaflets, lower surface: Close to 147B; venation, close to 148A.

*Petioles, leaves*.—Length: About 1.8 cm. Diameter: About 2 mm. Texture, upper surface: Prickly. Texture, lower surface: Smooth, glabrous. Color, upper surface: Close to 146C and 175D. Color, lower surface: Close to 146A to 146C.

*Petioles, leaflets*.—Length: About 2.3 cm. Diameter: About 1.3 mm. Texture, upper surface: Prickly. Texture, lower surface: Smooth, glabrous. Color, upper surface: Close to N186C and 146A. Color, lower surface: Close to 144A and 146A.

*Stipules*.—Arrangement and appearance: Two, adnate to the petiole, leafy in appearance. Length: About 2.5 cm. Width: About 2.5 mm. Shape: Roughly deltoid.

Apex: Acuminate, tapered. Base: Truncate. Margin: Serrate. Texture, upper and lower surfaces: Irregularly pubescent; membranous. Venation pattern: Pinnate. Color, upper surface: Close to 137A and 146A. Color, lower surface: Close to 146A.

Flower description:

*Flower type and flowering habit*.—Symmetrical rosette flowers; flowers typically grown as spray types; flowers face upright.

*Flowering season*.—Plants of the new Rose flower year-round under greenhouse conditions; early flowering habit, plants begin flowering about 86 days after pinching; in the garden, optimal flowering from spring through autumn; flowering intermittent.

*Spray height*.—About 25 cm.

*Spray diameter*.—About 23 cm.

*Quantity of flowers per spray*.—About seven.

*Flower diameter*.—About 6.7 cm.

*Flower depth* (*height*).—About 2.7 cm.

*Flower longevity on plant*.—About 26 days; flowers persistent.

*Flower longevity as a cut flower*.—Excellent postproduction longevity, flowers last about ten to twelve days.

*Fragrance*.—Fragrant, pleasant.

*Flower buds*.—Shape: Ovoid. Length: About 2.8 cm. Diameter: About 2.2 cm. Color: Close to 146B becoming closer to 175A with development.

*Petals*.—Quantity: About 27 to 30 per flower; petals imbricate. Length: About 3.1 cm. Width: About 3.7 cm. Shape: Nearly round; transversely ovate. Apex: Blunt to shortly acute. Base: Obtuse. Margin: Entire. Texture, upper and lower surfaces: Smooth, glabrous; papery to coriaceous. Color: When opening, upper surface: Close to 44A; towards the base, close to 7A. When opening, lower surface: Close to 39A; towards the base, close to 7D. Fully opened, upper surface: Close to between 40A and 44B; towards the base, close to 160B. Fully opened, lower surface: Close to 41B; towards the base, close to 150D.

*Petaloids*.—Quantity: About five; petaloids whorled. Length: Variable. Width: Variable. Shape: Irregularly shaped. Apex: Blunt to shortly acute. Base: Obtuse. Margin: Entire or uneven. Color: When opening and fully opened, upper surface: Close to 43A, 157A and 153C. When opening and fully opened, lower surface: Close to 41A, 155B and 153D.

*Sepals*.—Quantity per flower: Typically five in a single whorl. Length: About 3.6 cm. Width: About 1.3 cm. Shape: Roughly deltoid. Apex: Tapered. Base: Truncate. Margin: Entire; ciliate and/or glandular. Texture, upper surface: Pubescent; leathery. Texture, lower surface: Glandular; irregularly pubescent along the margins; leathery. Color: When opening, upper surface: Close to 146B to 146C. When opening, lower surface: Between 144A and 146A and 175B. Fully opened, upper surface: Between 145B and 146B. Fully opened, lower surface: Close to 146B and 178A.

*Pedicels*.—Length: About 3.7 cm. Diameter: About 2.9 mm. Strength: Strong. Aspect: About 38° from vertical. Texture: Spiny, glandular. Color: Close to 146B and N199B.

*Reproductive organs*.—Stamens: Quantity: About 115 per flower. Anther length: About 2.8 mm. Anther shape: Reniform. Anther color: Close to 153D and 163B. Filament color: Close to 12A and 33B. Pollen amount: Scarce. Pollen color: Close to 163A. Pistils: Quantity: About 90 per flower. Pistil length: About 1.2 cm. Stigma shape: Broadly reniform. Stigma color: Close to 153D. Style length: About 8.7 mm. Style color: Close to 157C. Receptacle height: About 9 mm. Receptacle diameter: About 8 mm. Receptacle shape: Cup-shaped. Receptacle texture: Smooth, glabrous. Receptacle color: Close to 144B and 165A. Seeds and fruits: Seed and fruit development have not been observed on plants of the new Rose.

Pathogen & pest resistance/tolerance: Plants of the new Rose have been observed to resistant to *Botrytis*. Plants of the new Rose have not been observed to be resistant to pests and other pathogens common to Rose plants.

Temperature tolerance: Plants of the new Rose have been observed to tolerate temperatures ranging from 0° C. to 35° C.

It is claimed:

1. A new and distinct Rose plant named 'Esm R059' as illustrated and described.

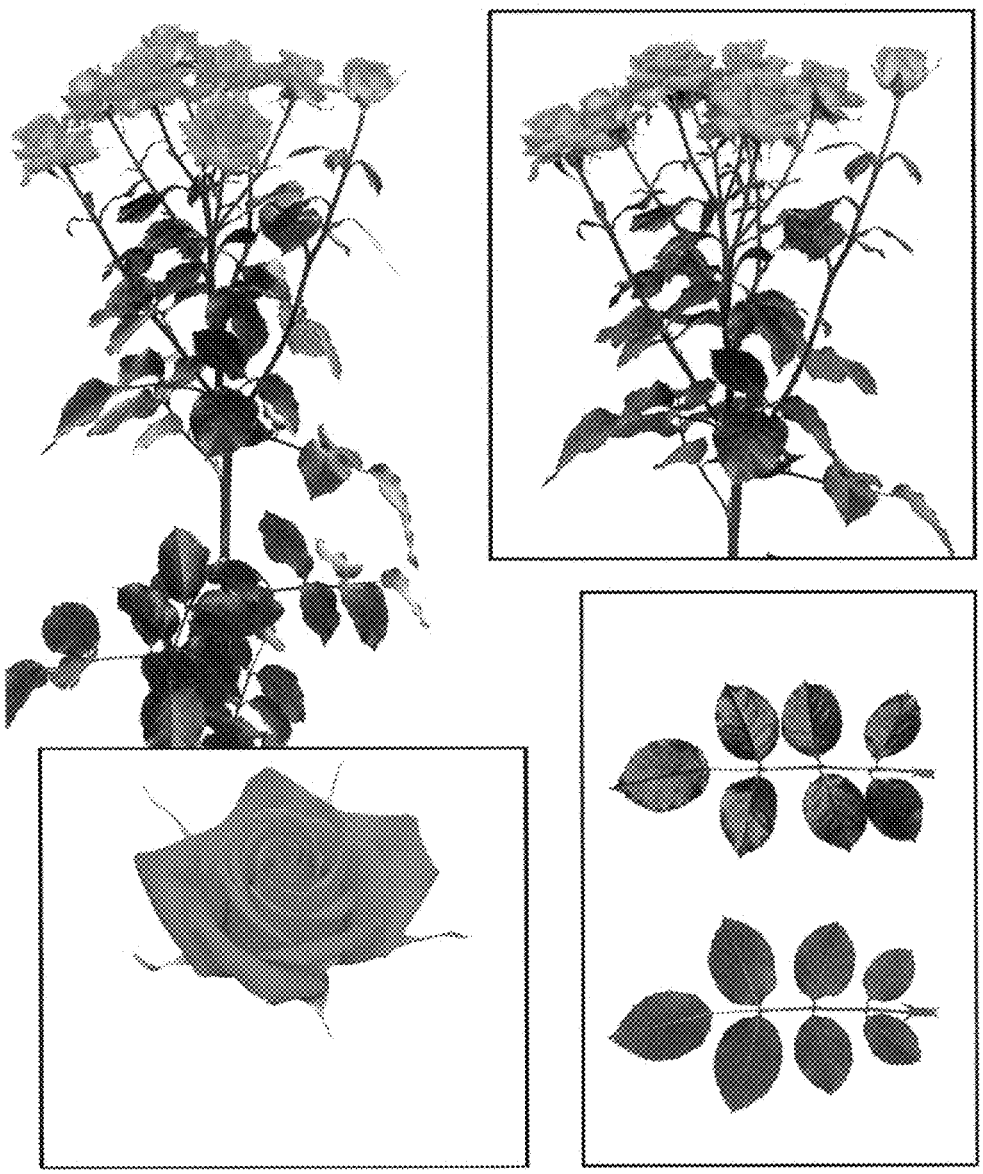

* * * * *